US00PP15966P3

(12) United States Plant Patent
Trees

(10) Patent No.: US PP15,966 P3
(45) Date of Patent: Sep. 20, 2005

(54) ***GAILLARDIA* PLANT NAMED 'BALTORYELL'**

(50) Latin Name: *Gaillardia pulchella*
Varietal Denomination: Baltoryell

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 133 days.

(21) Appl. No.: 10/741,704

(22) Filed: Dec. 19, 2003

(65) Prior Publication Data

US 2005/0138709 P1 Jun. 23, 2005

(51) Int. Cl.[7] ..... A01H 5/00

(52) U.S. Cl. ..... Plt./226

(58) Field of Search ..... Plt./226

*Primary Examiner*—Kent Bell
(74) *Attorney, Agent, or Firm*—Wood, Phillips, Katz, Clark & Mortimer

(57) ABSTRACT

A new and distinct cultivar of *Gaillardia* plant named 'Baltoryell', characterized by its yellow-colored ray florets, light green disc florets and vigorous, upright, and mounded growth habit.

2 Drawing Sheets

Latin name of genus and species of plant claimed: *Gaillardia pulchella.*
Variety denomination: 'Baltoryell'.

BACKGROUND OF THE INVENTION

The present invention relates to a new and distinct cultivar of *Gaillardia* plant botanically known as *Gaillardia pulchella* and hereinafter referred to by the cultivar name 'Baltoryell'.

The new cultivar originated as the product of the open-pollination, in November 1999, of the proprietary breeding selection designated 'NCT-137-2' (not patented) with a mix of pollen from plants grown from Thompson & Morgan double *Gaillardia* mix (not patented). The new *Gaillardia* was discovered and selected as a single flowering plant within the progeny of the above stated open-pollination during October 2000 at Arroyo Grande, Calif.

Asexual reproduction of the new cultivar by terminal stem cuttings taken since November 1999 at Arroyo Grande, Calif. and West Chicago, Ill. has demonstrated that the new cultivar reproduces true to type, with all the characteristics as herein described, firmly fixed and retained through successive generations of such asexual propagation.

SUMMARY OF THE INVENTION

It was repeatedly found that the cultivar of the present invention:

1. Forms yellow-colored ray florets and light green-colored disc florets, and
2. Exhibits a vigorous, upright, and mounded plant habit.

'Baltoryell' has not been observed under all possible environmental conditions to date. Accordingly, it is possible that the phenotype may vary somewhat with variations in the environment such as temperature, light intensity, and day length without, however, any variation in genotype.

'Baltoryell' is distinguished from its female parent primarily in inflorescence color.

Of the *Gaillardia* cultivars known to the inventor, the most similar to 'Baltoryell' is 'Sundance' (not patented). However, in side-by-side comparisons, plants of the new cultivar differ from plants of 'Sundance' primarily in inflorescence color.

BRIEF DESCRIPTION OF THE PHOTOGRAPHS

The accompanying photographs show as nearly true as it is reasonably possible to make the same in color illustrations of this type, typical inflorescence and foliage characteristics of the new cultivar. The plants were grown for 12 weeks in a greenhouse at West Chicago, Ill.

DETAILED BOTANICAL DESCRIPTION

Figure 1:
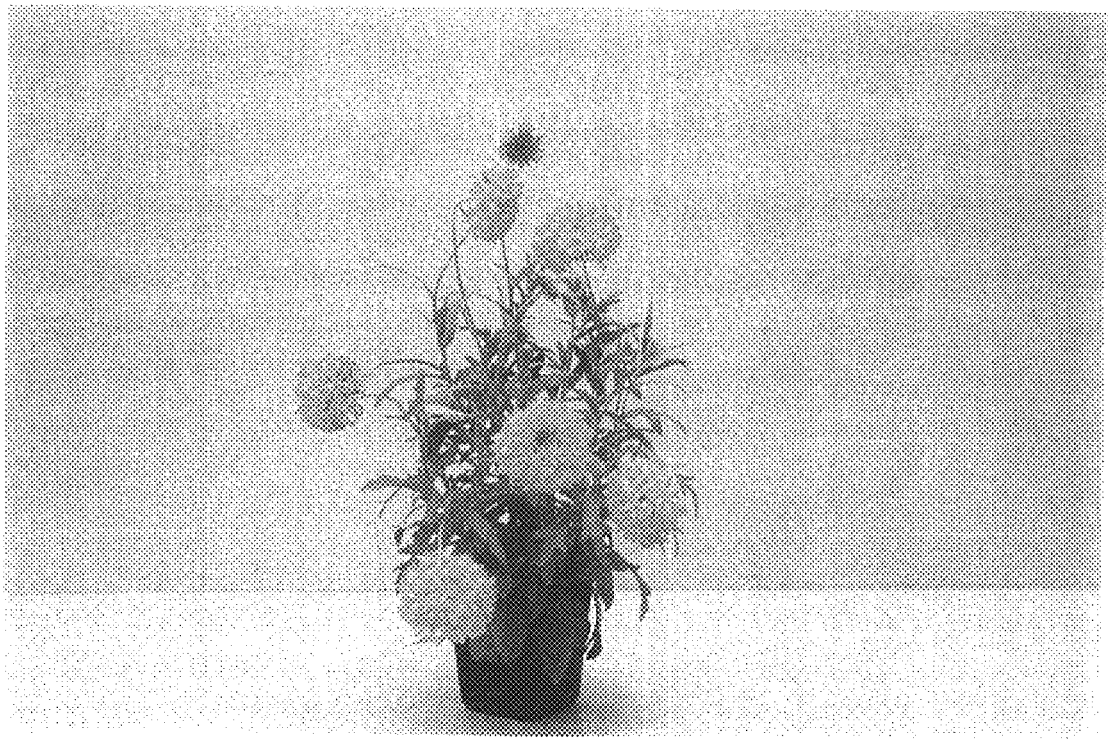
FIG. 1 illustrates the overall growth and flowering habit of 'Baltoryell'.
Figure 2:
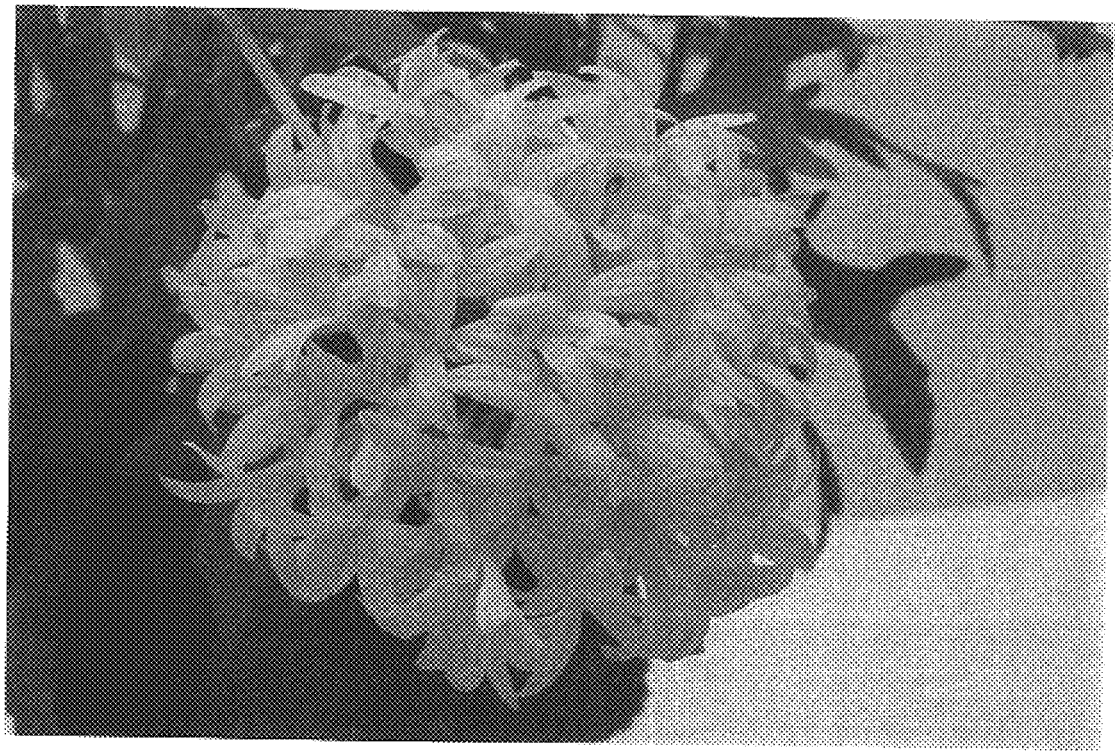
FIG. 2 illustrates a fully opened inflorescence of 'Baltoryell'.
Figure 3:
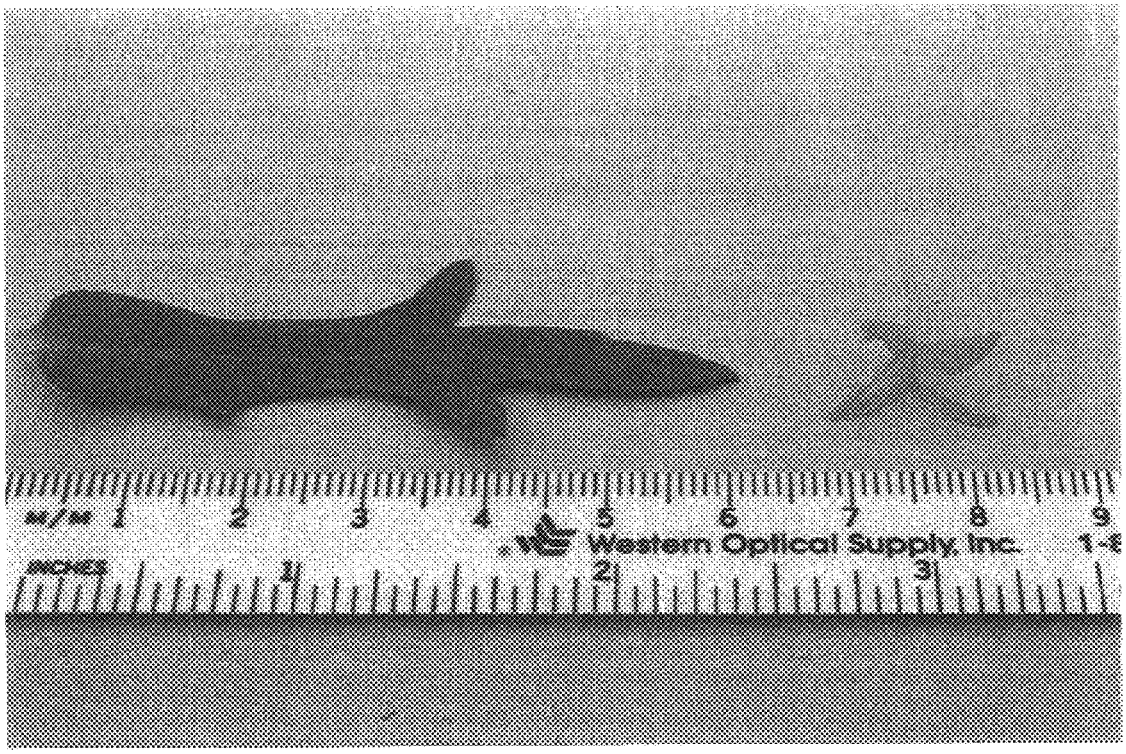
FIG. 3 illustrates a close-up view of a single ray floret and leaf of 'Baltoryell'.

The chart used in the identification of colors described herein is The R.H.S Colour Chart of The Royal Horticultural Society, London, England 1995 edition, except where general terms of ordinary significance are used. The color values were determined on May 21, 2003 in West Chicago, Ill. The readings were taken between 10:00 and 11:45 a.m. under natural daylight conditions. The plants were produced from cuttings taken from stock plants and were grown in a double polycarbonate-covered greenhouse in West Chicago, Ill. under conditions comparable to those used in commercial practice. The plants were grown in 10 cm pots while utilizing a soilless growth medium. Greenhouse temperatures were maintained at approximately 65°–75° F. (18°–24° C.) during the day and approximately 60° 65° F. (15°–18° C.) during the night. Greenhouse light levels of 5,000–8,000 footcandles were maintained during the day. Plants were pinched at three weeks after planting. The following measurements and descriptions were taken at 12 weeks after planting of rooted cuttings.

Botanical classification: *Gaillardia pulchella* cultivar 'Baltoryell'.

Parentage:

*Female parent.*—Proprietary *Gaillardia pulchella* selection designated 'NCT-137-2' (not patented).

*Male parent.*—Mix of pollen from plants grown from Thompson & Morgan double *Gaillardia* mix (not patented).

Propagation:

*Type cutting.*—Terminal stem.

*Time to initiate roots.*—Approximately 5 to 8 days.

*Time to develop roots.*—Approximately 21 to 28 days.

*Root description.*—Fibrous and well branched.

Plant description:

*General appearance and form.*—Upright, mounded and vigorous.

*Crop time.*—Approximately 6–7 weeks from planting of rooted cuttings.

*Height from soil level to top of blooms.*—Approximately 33.6 cm.

*Diameter (area of spread).*—Approximately 34.9 cm.

*Branching habit.*—Freely basal branching.

*Branch description.*—Quantity per plant: Approximately 4. Length: Approximately 20.6 cm. Diameter: Approximately 3 mm. Color: 146B. Texture: Smooth. Internode length: Approximately 2.5 cm.

*Foliage.*—Type: Simple. Arrangement: Opposite. Quantity per branch: Approximately 12. Venation pattern: Pinnate. Texture of upper and lower surface: Densely pubescent. Color of mature foliage: Upper surface: 138A with venation of 145C. Lower surface: Slightly lighter than 137C with venation of 145C. Upper leaves: Shape: Oblanceolate. Margin: Entire. Base: Sessile. Length: Approximately 4.6 cm. Width: Approximately 8 mm. Lower leaves: Shape: Spatulate. Margin: Pinnately lobed. Base: Sessile. Length: Approximately 5.6 cm. Width: Approximately 1.9 cm.

Flowering description:

*Outdoor flowering habit.*—'Baltoryell' is freely flowering under outdoor growing conditions with substantially continuous blooming from spring through fall.

Inflorescence description:

*Type/appearance.*—Solitary, composite, persistent. Disc and ray florets develop acropetally on a capitulum. Shape: Hemispherical.

*Fragrance.*—Faint, sweet.

*Quantity per plant.*—4 open inflorescences and 17 buds at any one time.

*Size.*—Diameter: Approximately 5 cm. Depth/height: Approximately 4.1 cm.

*Receptical.*—Shape: Hemispherical. Diameter: Approximately 2.2 cm. Depth/height: 5 mm.

*Bud.*—Shape: Oblate. Before first color: Diameter: Approximately 7.4 mm. Depth: Approximately 1.4 cm. Color: 151B. At first color: Diameter: Approximately 1.2 cm. Depth: Approximately 2.5 cm. Color: 1C.

*Ray florets.*—Quantity: Approximately 98 per inflorescence. Shape: Funnelform with 4 free lobes. Corolla diameter: 1.6 cm. Lobe length from tube: Approximately 5 mm. Lobe width: Approximately 4 mm. Lobe apex: Pointed to slightly rounded. Lobe margin: Entire. Lobe texture: Glabrous. Color of mature lobe: Upper surface: 5A with venation of 144B. Lower surface: 5C with venation of 144B. Corolla tube: Length: 2.1 cm. Diameter at apex: 4 mm. Diameter at base: 1 mm. Texture: Sparsely pubescent. Color: Fully opened, outer surface: 5C with venation of 144B and base of 145C. Inner surface: 5A.

*Disc florets.*—Quantity: Approximately 95. Shape: Funnelform. Lobe shape: Linear. Lobe apex: Long, acuminate. Length: 7 mm. Diameter: 3 mm. Texture of corolla tube: Outer surface: Densely pubescent. Inner surface: Glabrous. Color of apex: Lighter than 144B. Color of base: 149D, transparent.

*Peduncle.*—Strong, erect. Length: Approximately 12.5 cm. Diameter: Approximately 1.5 mm. Texture: Densely pubescent. Color: 146B.

*Phyllaries.*—Quantity: Approximately 30. Shape: Lanceolate. Apex: Acute. Base: Truncate. Margin: Entire. Length: 1 cm. Width at base: 2 mm. Texture: Densely pubescent. Color of upper and lower surfaces: 138A.

Reproductive organs:

*Androecium.*—On disc florets only. Stamen number: 4. Anther shape: Linear. Anther length: Approximately 3 mm. Anther width: Approximately 0.08 mm. Anther color: 1C. Filament Length: 3.5 mm. Filament color: 149D. Amount of pollen: Abundant. Pollen color: 13A.

*Gynoecium.*—On disc and ray florets. Pistil length: Approximately 9 mm. Stigma shape: Narrow lanceolate, densely pubescent. Stigma length: Approximately 4 mm. Stigma color: 145A. Style length: 4.5 mm. Style color: 149D. Ovary length: 0.5 mm. Ovary color: 144D.

Seed and fruit production: Neither seed nor fruit production has been observed.

Disease and pest resistance: Resistance to pathogens or pests common to *Gaillardia* has not been observed.

Hardiness zone: 'Baltoryell' is hardy in zones nine (9) and above.

What is claimed is:

1. A new and distinct cultivar of *Gaillardia* plant named 'Baltoryell' substantially, as herein shown and described, which:

1. Forms yellow-colored ray florets and light green disc florets, and
2. Exhibits a vigorous, upright, and mounded growth habit.

* * * * *